United States Patent
Seo et al.

(10) Patent No.: US 10,624,611 B2
(45) Date of Patent: Apr. 21, 2020

(54) DYNAMIC POWER DOPPLER IMAGING IN ULTRASOUND

(71) Applicant: Siemens Medical Solutions USA, Inc., Malvern, PA (US)

(72) Inventors: Chi Hyung Seo, Sammamish, WA (US); King Yuen Wong, Issaquah, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1184 days.

(21) Appl. No.: 14/473,652

(22) Filed: Aug. 29, 2014

(65) Prior Publication Data
US 2016/0058421 A1    Mar. 3, 2016

(51) Int. Cl.
A61B 8/06    (2006.01)
A61B 8/08    (2006.01)
A61B 8/00    (2006.01)

(52) U.S. Cl.
CPC .............. *A61B 8/488* (2013.01); *A61B 8/06* (2013.01); *A61B 8/461* (2013.01); *A61B 8/483* (2013.01); *A61B 8/5207* (2013.01); *A61B 8/5223* (2013.01)

(58) Field of Classification Search
USPC .................................................. 600/453
See application file for complete search history.

(56) References Cited

U.S. PATENT DOCUMENTS

| | | | |
|---|---|---|---|
| 5,148,809 A | 9/1992 | Biegeleisen-Knight et al. | |
| 5,446,800 A * | 8/1995 | Briggs | G01S 7/52071 382/128 |
| 5,615,679 A | 4/1997 | Ri et al. | |
| 6,468,213 B1 * | 10/2002 | Knell | A61B 8/00 600/437 |
| 6,728,566 B1 * | 4/2004 | Subramanyan | G06T 11/005 600/407 |
| 7,231,243 B2 * | 6/2007 | Tearney | A61B 1/00082 600/407 |
| 7,682,311 B2 | 3/2010 | Simopoulos et al. | |
| 8,478,387 B2 * | 7/2013 | Xu | A61B 5/0066 600/477 |
| 2003/0216621 A1 * | 11/2003 | Alpert | A61B 5/0215 600/300 |
| 2005/0283075 A1 * | 12/2005 | Ma | G06T 15/08 600/441 |
| 2006/0052698 A1 * | 3/2006 | Loupas | A61B 8/06 600/437 |
| 2007/0066896 A1 * | 3/2007 | Simopoulos | G01S 15/584 600/437 |

OTHER PUBLICATIONS

"3. Spectra" Retrieved from http://msp.ucsd.edu/syllabi/170.13f/course-notes/node3.html (Year: 2014).*

* cited by examiner

Primary Examiner — Luther Behringer

(57) ABSTRACT

For Doppler imaging in ultrasound, a single parameter is formed from both power and velocity. In any combination function, a derivative of velocity and/or velocity are combined with power. The resulting value is used to look-up a color from a one-dimensional color map.

19 Claims, 3 Drawing Sheets

DYNAMIC POWER DOPPLER IMAGING IN ULTRASOUND

BACKGROUND

This present embodiments relate to Doppler imaging in ultrasound. Conventional power Doppler mode imaging achieves high sensitivity by using high temporal filtering. As a result, flow dynamics are reduced, resulting in a dull look that may be of less diagnostic value to the user. Also because of spatial filtering, power Doppler may not clearly represent the border between the blood vessel images and the background. As a result, it may be difficult for the viewer to identify small blood vessels accurately.

Directional power or convergent power Doppler incorporates velocity information with the power information using a 2-dimensional color map. The power and velocity information are used as input indices for looking up color values for an image. Although these techniques are able to present flow dynamics, they lack the sensitivity of pure power Doppler. Moreover, it is in general more difficult for a user to decipher multidimensional information from a color map than one-dimensional information such as only velocity or power. In another approach, a derivative of power is used to enhance the imaging. Although this technique has similar sensitivity to traditional power Doppler, the temporal flow dynamics may be missing.

BRIEF SUMMARY

By way of introduction, the preferred embodiments described below include a method, system, computer readable medium, and instructions for Doppler imaging in ultrasound. A single parameter is formed from both power and velocity. In any combination function, a derivative of velocity and/or velocity are combined with power. The resulting value is used to look-up a color from a one-dimensional color map.

In a first aspect, a method is provided for Doppler imaging in ultrasound. An ultrasound scanner acquires ultrasound data representing a region of a patient. A Doppler processor estimates powers and velocities from the ultrasound data for respective locations in the region. Spatial derivatives of the velocities are calculated. The spatial derivatives of the velocity and the powers are combined. The results of the combination map to colors. An image of the region is generated from the colors.

In a second aspect, a non-transitory computer readable storage medium has stored therein data representing instructions executable by a programmed processor for Doppler imaging in ultrasound. The storage medium includes instructions for: calculating spatial gradients for the velocity values; summing the spatial gradients, the power values, and the velocity values; mapping results of the summing to color values; and generating a color flow image with the color values.

In a third aspect, a system is provided for Doppler imaging in ultrasound. A transducer and beamformer for scanning a scan region are provided. A Doppler estimator is configured to estimate energy and velocity samples of the scan region at different locations. A processor is configured to calculate, for each of the different locations, a value of a parameter with a function having the energy and derivatives of velocity samples as variables. A memory is configured to store a one-dimensional map of colors indexed by the parameter.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Dynamic power Doppler imaging is provided. Dynamic power Doppler imaging attains the sensitivity of power Doppler while retaining dynamic information of velocity Doppler. Unlike existing directional power or convergent color Doppler, which incorporate velocity information as a 2-dimensional color map, the velocity and power information are combined to form a parameter. The parameter is a function of the momentum (e.g., combination of power and velocity), a function of power and velocity gradient, or any combination of power and velocity. As a result, spatial and temporal velocity profiles may be visualized as flow intensity varies in the image spatially and temporally, while maintaining high sensitivity to blood flow.

In various embodiments, a color Doppler parameter is derived from any weighted combination of (1) power and spatially high pass filtered velocity (i.e. gradient), (2) power and velocity, or (3) power, velocity and spatially high pass filtered velocity. In addition, optionally, spatial filtering, such as anti-aliasing/phase unwrapping, is performed to obtain accurate velocity information before combination. Another additional option includes further spatial filtering applied to the derived parameter to minimize discontinuities before color mapping.

Figure 1:
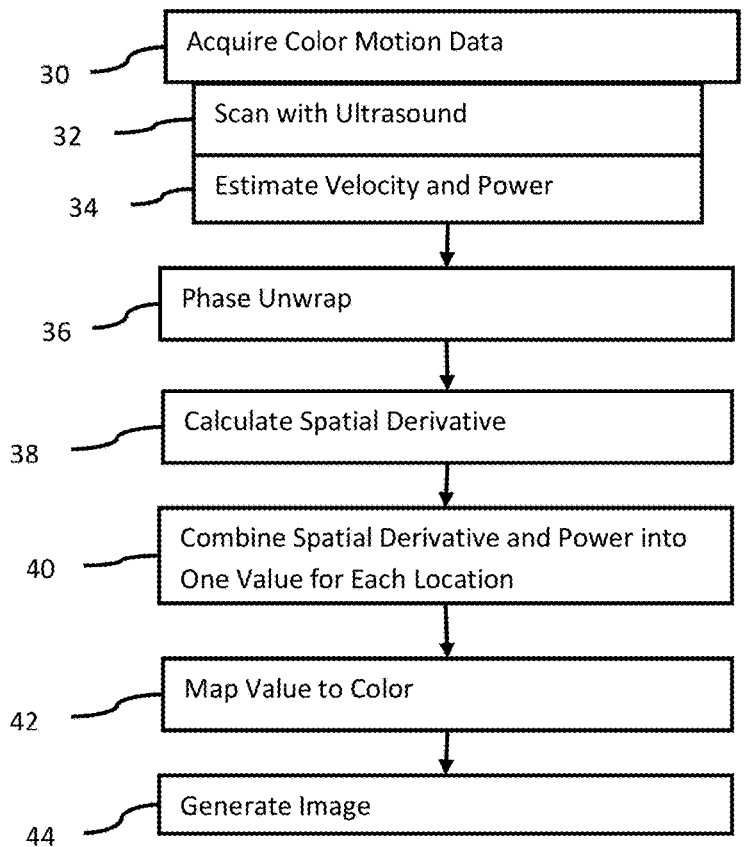
FIG. 1 is a flow chart of one embodiment of a method for Doppler imaging in ultrasound.

FIG. 1 shows a method for Doppler imaging in ultrasound. The method is performed by the ultrasound imaging system 10 of FIG. 3, the processor 24, or a different system and/or processor. For example, the ultrasound imaging system 10 acquires, phase unwraps, calculates, combines, maps, and generates an image. As another example, an ultrasound system 10 acquires ultrasound data and uses a Doppler processor to estimate the velocity and power, and the processor 24 performs the other acts or sub-sets of the other acts. The processor 24 may control other components to provide information and/or interact to perform any one or more of the acts. The system 10 and/or processor 24 are configured by instructions or a program for performing the acts.

The acts of FIG. 1 are performed in the order shown or a different order. Additional, different, or fewer acts than shown in FIG. 1 may be used. For example, phase unwrapping of act 36 is not performed, such as where the velocity scale is set conservatively in view of the flow being imaged.

In another example, an image is not generated in act 44, and the image data mapped to color is instead stored or used for calculating a value.

In act 30, color flow or flow ultrasound data is acquired. Color flow data includes estimates of velocity, energy (e.g., power), and/or variance. In one embodiment, at least velocity and power are estimated. To estimate the color flow, data representing blood, fluid, or flow of the patient is acquired. In alternative embodiments, tissue motion data is acquired, such as estimates of velocity, energy, and/or variance of tissue motion. Any motion data, whether from flow or tissue movement, may be acquired. Color flow data is used in examples below, but may alternatively or additionally be tissue motion data.

The color flow data is acquired by transfer over a network, loading from memory, and/or by scanning a patient in act 32. For transfer or loading, data previously acquired by scanning is acquired. In one embodiment using an ultrasound system, a patient or region is scanned in act 32 in real-time with the imaging. The scanned region is an interior of an object, such as the patient. The scan is of a volume, plane, or line region. Scanning a plane provides data representing different locations or samples of the plane. The data representing the region is formed from spatial sampling of the object. The spatial samples are for locations distributed in an acoustic sampling grid.

The region for the color flow data scan is a region of interest smaller than a field of view or for the entire field of view. The ultrasound system may scan the field of view using B-mode imaging. The color flow region is a sub-set of that field of view. The user or a processor determines the region of interest in which color flow scanning occurs.

Spatial samples along one or more scan lines are received. Where the transmit beam insonifies just one receive scan line, then samples along that scan line are received. Where the transmit beam insonifies multiple scan lines, then samples along the multiple scan lines are received. To generate the samples for different receive beams, parallel receive beamformation is performed so that the different receive beams are sampled at a same time. For example, a system may be capable of forming two or more, tens or hundreds of receive beams in parallel. Alternatively, signals received from the elements are stored and sequentially processed. Spatial samples are acquired for a plurality of receive lines in the region of interest in response to one and/or in response to sequential transmit beams.

The scanning may be performed a plurality of times to cover the region. The acts are repeated to scan different portions of the region of interest. Alternatively, performing the acts once acquires the data for the entire region of interest.

The complete region of interest is scanned multiple times at different times. Scanning at different times acquires spatial samples associated with flow or motion. Any now known or later developed pulse sequences may be used. A sequence of at least two (flow sample count) transmissions is provided along each scan line. Any pulse repetition frequency, flow sample count, and pulse repetition interval may be used. The echo responses to the transmissions of the sequence are used to estimate velocity, energy (power), and/or variance at a given time in act 34. The transmissions along one line(s) may be interleaved with transmissions along another line(s). With or without interleaving, the spatial samples for a given time are acquired using transmissions from different times. The estimates from different scan lines may be acquired sequentially, but rapidly enough to represent a same time from a user perspective. Multiple scans are performed to acquire estimates for different times.

The received spatial samples may be clutter filtered. The clutter filtering is of signals in the pulse sequence for estimating motion at a given time. A given signal may be used for estimates representing different times, such as associated with a moving window for clutter filtering and estimation. Different filter outputs are used to estimate motion for a location at different times.

Color flow data or tissue motion data is generated in act 34 from the spatial samples. Any motion data may be generated, such as velocity, energy (power), and/or variance. Doppler processing, such as autocorrelation, may be used. In other embodiments, temporal correlation may be used. Another process may be used to estimate the flow data. Color Doppler parameter values (e.g., velocity, energy, or variance values) are estimated from the spatial samples acquired at different times. "Color" is used to distinguish from spectral Doppler imaging, where the power spectrum for a range gate is estimated. The change in frequency (e.g., Doppler shift) between two samples for the same location at different times indicates the velocity. A sequence of more than two samples may be used to estimate the color Doppler parameter values. Estimates are formed for different groupings of received signals, such as completely separate or independent groupings or overlapping groupings. The estimates for each grouping represent the spatial location at a given time.

The estimation is performed for the different sampled spatial locations. For example, velocities for the different locations in a plane are estimated from echoes responsive to the scanning. Multiple frames of flow data may be acquired to represent the region of interest at different times, respectively.

The estimates may be thresholded. Thresholds are applied to the velocities and/or powers. For example, a low velocity threshold is applied. Velocities below the threshold are removed or set to another value, such as zero. As another example, where the energy is below a threshold, the velocity value for the same spatial location is removed or set to another value, such as zero. Alternatively, the estimated velocities are used without thresholding.

The power and/or velocity data may be filtered, such as spatial and/or temporal filtered. The same or different filters are applied to velocities as compared to powers. In one embodiment, the velocities are not temporally filtered or are temporally filtered slightly while the powers are temporally filtered to a greater extent. Other processing may be applied. The acquired motion data is a frame of data or image representing the patient at a given time, despite being estimated from received signals over a flow sample count.

In act 36, the velocities are phase unwrapped. If the velocity scale is set such that some of the velocities are aliased, the aliasing is removed by phase unwrapping. The unwrapping occurs prior to calculating the spatial derivative of the velocities in act 38 and/or the combination using the velocities in act 40.

The phase unwrapping corrects the velocities, such as adding or removing phase by $2\pi$. Any phase unwrapping may be used. Sign changes, amplitude, spatial variance, or other information may be used to identify aliased values. The phase unwrapping is applied to the aliased values.

The phase unwrapping produces unaliased or corrected velocity information. The velocities with little to no temporal filtering provide dynamic flow information. As such, the phase unwrapped velocities contain the blood flow dynamics in accordance with the cardiac cycle or other flow variation.

In act 38, spatial derivatives of the velocities are calculated. The two or three-dimensional distribution of velocities is used to determine a two or three-dimensional distribution of spatial derivatives of velocity. The local spatial derivative around each location is calculated. Any size kernel may be used for determining a spatial derivative for a given location, such as three samples with a middle sample being the location and the other two samples being immediately adjacent samples on opposite sides along a line. One or more spatial gradients are calculated for each location, such as the spatial gradients along one, two, or more directions (e.g., along x and y dimensions in a Cartesian coordinate system). Where the gradients are determined along more than one direction, the gradient for the location may be a sum or average of the gradients. Other functions, such as a maximum selection, may be used to determine the spatial derivative for a given location. Two or three dimensional gradient calculation may be used.

In act 40, the powers are combined with the spatial derivatives of the velocities. The combination forms a parameter value. Different parameters, such as power and spatial derivative of velocity, are combined into one parameter. Values of multiple variables are used to calculate a single value for a given location. The parameter value is calculated for each of the locations. Using both the spatial derivative and the power in a parameter for imaging, a more three-dimensional looking image may be created while keeping the blood flow dynamics. Visualization of vessel boundary may also be improved because of the use of the spatial derivative.

Any combination function may be used. Multiplication, division, maximum selection, minimum selection, averaging, and/or other combinations may be used. In one embodiment, summation is used. The power and the spatial derivative for each location are summed. The sum may be divided to create an average or not.

Any number of variables may be used in the combination function. In one embodiment, the power and the spatial derivative are used without other velocity information. In another embodiment, the power, the spatial derivative of velocity, and the velocity are used.

The combination is a mathematical operation. A processor calculates the value of the combination parameter from the values of the variables. In another implementation, a look-up table indexed by the values of the variables is used to perform the calculation.

Conventional power mode uses the power for imaging. The original power, $p_0$, is used. Instead of using just power, the power is combined with information representing the dynamics of the flow. The normal power is combined with the spatial gradient on the phase unwrapped velocity information to yield topographic information. Below is one example combination of power with spatial derivative:

$$p_2 = p_0 + \alpha \nabla v_{x,y} + \delta$$

where $\alpha$ is a weight, $v_{x,y}$ is the velocity in two-dimensions (x, y) and $\delta$ is an offset. Another combination using a summation combination uses the phase unwrapped velocity instead of the spatial derivative, as represented by:

$$p_3 = p_0 + \beta v_{x/y} - \delta$$

where $\beta$ is a weight. Yet another combination using summation includes both the spatial derivative of velocity and the velocity, as represented by:

$$p_4 = p_0 + \alpha \nabla v_{xy} + \beta v_{x/y} + \delta$$

Other combinations may be used.

In the example combinations above or other combinations, the relative contribution of the power, spatial derivative of velocity, and/or velocity is set using one or more weights. By weighting one variable, the relative contribution between two variables is set. For a three variable summation, weighting two of the variables sets a relative contribution between the three variables. More or fewer weights may be used. In the example above, both the velocity and the spatial derivative of velocity are weighted by different weights. The same weights may be used. The weights are values other than 1. The values are integer or fractional. For example, the values are between 0 and 1. The same weights are used for the same variables for each location, but may vary spatially. By varying the weighting factors ($\alpha$ and $\beta$ in the example combination equations), varying degrees of apparent three-dimensional look and dynamic look may be provided.

The offset, $\delta$, keeps the velocity and/or spatial derivative of the velocity from making the parameter signed. Rather than being signed with positive and negative values like velocity, the parameter is calculated to be unsigned (e.g. only positive or only negative values) like power values. The values of the parameter are all negative or all positive rather than both negative and positive. The offset makes sure that the calculated parameter values do not go below a display threshold in order to retain the sensitivity of conventional power Doppler. The offset may also account for a noise floor, such as shifting the velocities or derivatives to have a lowest value above a positive noise floor (e.g., 10 or greater on a 0-255 dynamic range). In alternative embodiments, the values are signed or have positive and negative values. In yet other alternative embodiments, the absolute value of velocity or velocity shifted by adding or subtracting to be all positive or all negative are used for calculating the parameter without an offset in the combination function.

In one embodiment, the offset is determined as greater than a highest positive or highest negative value of the spatial derivatives and/or velocities. For example, the greatest magnitude negative velocity is −120. The offset is set to 120, 121, or greater number, shifting the velocities so that the −120 is at a zero level or higher. The greatest magnitude for the offset is either based on the dynamic range of values or on a sampling of the values themselves (e.g., 1-3 seconds worth of values).

The offset may account for weighting. The relative weighting is used in determining the offset. For example, $\alpha$ or $\beta$ is 0.5. Rather than using −121 in the example above, −61 is used by accounting for the weights effect (multiply the greatest magnitude by the weight). To keep the values of the calculated parameter positive or no lower than zero, the greatest magnitude multiplied by the corresponding weight is used to set the offset level.

In act 42, the calculated values of the parameter are mapped to colors. The results of the summing or other calculation from the power with velocity and/or spatial derivatives are used to look up red, green, blue (RGB) or other color values. Different values are mapped to different colors. Each different color is a different hue, intensity, and/or brightness. For example, shades of orange are used. Unlike a velocity map, the mapping represents all positive or all negative. The color map used is the same or similar to a power color map. Since a different parameter than power alone is being mapped, a different color map than power maps may be used. In alternative embodiments, the color map uses positive and negative values of the parameter, such as using shades of two colors, one for positive and another for negative.

The color map is a one-dimensional map. Rather than using two or more different values (e.g., velocity derivative and power) to look up a color, the calculated single value of the parameter is used. The colors map to a single parameter. In alternative embodiments, multi-dimensional color maps are used where one of the indices is the parameter and other indices are for other parameters or information.

In yet another embodiment, the combination function is incorporated into the color map. Using the power and velocity information as indices, the color for each location is determined from the two-dimensional color map. Unlike two-dimensional color mapping, the color map has color only associated with positive or only associated with negative values. Different colors are not used to reflect the indices differently.

In act 44, an image is generated. The image is a color flow image, such as an image formed using the colors from act 42. The color value for each location is based on the parameter value for that location. The image includes colors that represent dynamic information from velocities with little to no temporal filtering and represent powers that provide sensitivity.

The image may include other information. For example, the image is an overlay of the color flow data with B-mode data. For non-tissue locations or locations associated with sufficient flow, the color flow data (e.g., color mapped from the calculated parameter) are used to determine a color to display. For tissue locations or low/no flow locations, the B-mode data is used. The image represents the region of the patient scanned for color flow imaging, such as a region of interest in a B-mode field of view. The image for color Doppler may be the entire B-mode field of view. The entire image is color without any B-mode information or portions of the image include B-mode information.

Figure 2A:
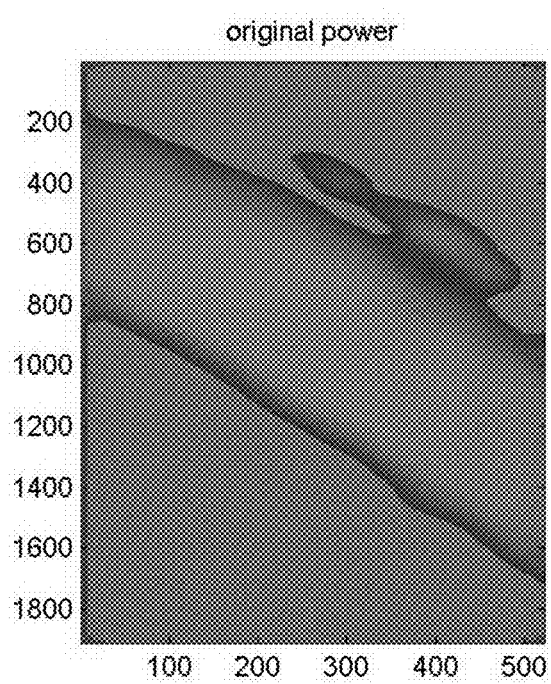
FIGS. 2A-D show example images with different combinations of power and velocity information.
Figure 2B:
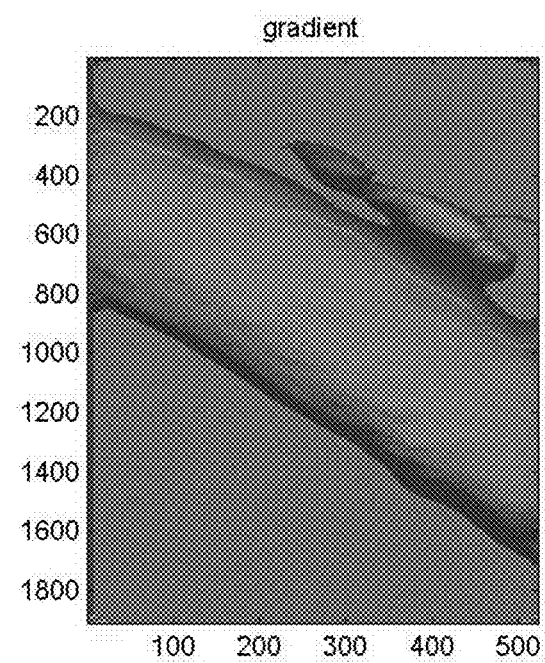
Figure 2C:
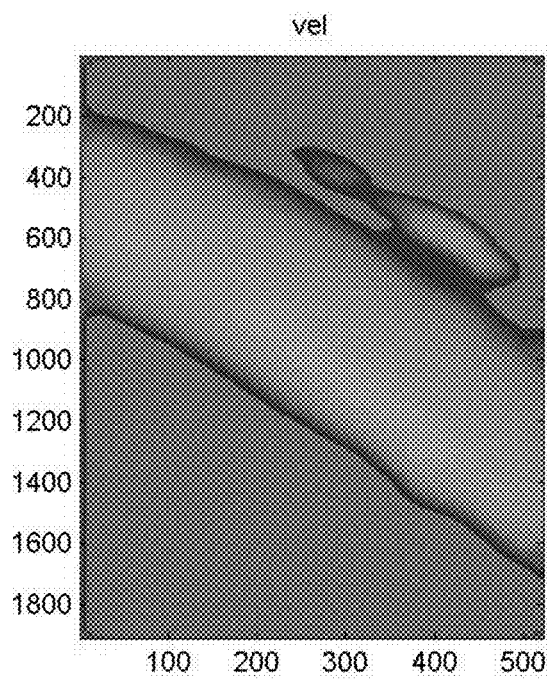
Figure 2D:
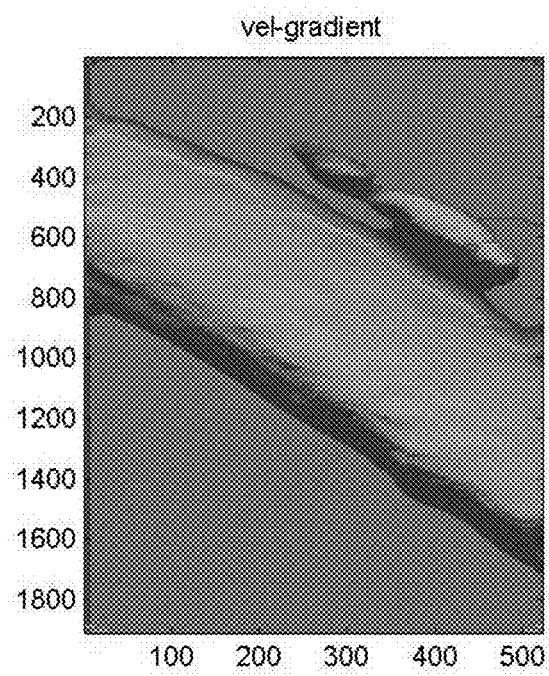

FIGS. 2A-D show example color flow images of a same vessel created in different approaches. FIG. 2A shows a power Doppler image where just power values are mapped to color. The edges of the vessel are darker due to less power. FIGS. 2B-D show using the parameter of power with other information mapped with the same color map. The combination is weighted to result in a similar dynamic range or use of similar colors as power alone. In the case of FIG. 2B, the power is combined with the gradient of velocity. The result is a more three-dimensional looking representation of the vessel as gradations or regions of change in velocity are highlighted in the power information. FIG. 2C shows the power combined with the velocity. Brighter colors are more prominent. In FIG. 2D, both velocity and gradient are combined with power. The combination of power with the velocity information may more clearly show the border of the vessel. For a real-time or other display over time, the combination of power with velocity information may better represent the dynamics of flow, such as showing shifts or changes more clearly.

Figure 3:
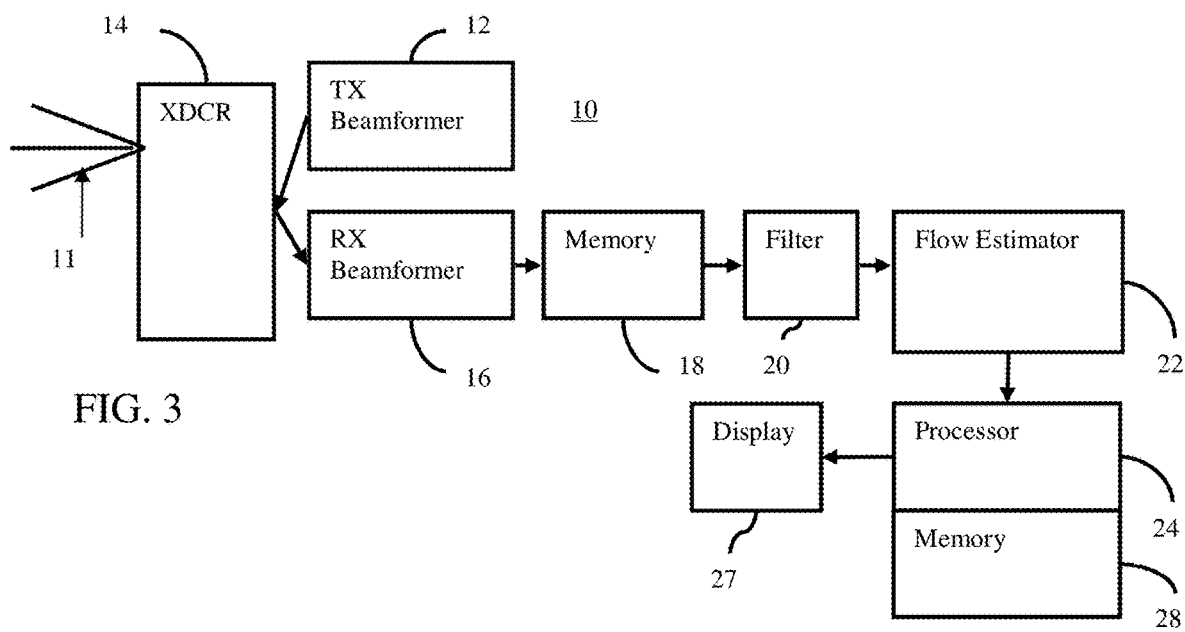
FIG. 3 is a block diagram of one embodiment of a system for Doppler imaging in ultrasound.

FIG. 3 shows one embodiment of a system 10 for Doppler imaging in ultrasound. The system 10 includes a transmit beamformer 12, a transducer 14, a receive beamformer 16, a memory 18, a filter 20, a flow estimator 22, a memory 28, a processor 24, and a display 27. Additional, different or fewer components may be provided. For example, the system includes a B-mode detector. As another example, the flow estimator 22 and processor 24 are provided without the front-end components, such as the transmit and receive beamformers 12, 16. In one embodiment, the system 10 is a medical diagnostic ultrasound system. In an alternative embodiment, the system 10 is a computer or workstation. In yet another embodiment, the flow estimator 22 is part of a medical diagnostic ultrasound system or other medical imaging system, and the processor 24 is part of a separate workstation or remote system, making of the ultrasound imaging system.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams to scan a region. Vector®, sector, linear or other scan formats may be used. The receive lines and/or transmit beams are distributed in the scan region. The receive beamformer 16 samples the receive beams at different depths. Sampling the same location at different times obtains a sequence for flow estimation.

In one embodiment, the transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and/or combinations thereof. A transmit beam focus is generated based on these beamforming parameters.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. In one embodiment, the beamform summer is configured to sum in-phase and quadrature channel data in a complex manner such that phase information is maintained for the formed beam. Alternatively, the beamform summer sums data amplitudes or intensities without maintaining the phase information.

The receive beamformer 16 is operable to form receive beams in response to the transmit beams. For example, the receive beamformer 16 receives one, two, or more receive beams in response to each transmit beam. The receive beams are collinear, parallel and offset or nonparallel with the corresponding transmit beams. The receive beamformer 16 outputs spatial samples representing different spatial locations of a scanned region. Once the channel data is beamformed or otherwise combined to represent spatial locations along the scan lines 11, the data is converted from the channel domain to the image data domain. The phase rotators, delays, and/or summers may be repeated for parallel receive beamformation. One or more of the parallel receive beamformers may share parts of channels, such as sharing initial amplification.

For imaging motion, such as tissue motion or fluid velocity, multiple transmissions and corresponding receptions are performed for each of a plurality of substantially same spatial locations. Phase changes between the different receive events for each given location indicate the velocity of the tissue or fluid. A velocity sample group corresponds to multiple transmissions for each of a plurality of scan lines 11. The number of times a substantially same spatial location, such as a scan line 11, is scanned within a velocity sample group is the velocity sample count. The transmissions for different scan lines 11, different velocity sample groupings or different types of imaging may be interleaved. The amount of time between transmissions to a substantially same scan line 11 within the velocity sample count is the pulse repetition interval or pulse repetition frequency. Pulse repetition interval is used herein, but includes the pulse repetition frequency.

The memory 18 is video random access memory, random access memory, removable media (e.g. diskette or compact disc), hard drive, database, corner turning memory or other memory device for storing data or video information. In one embodiment, the memory 18 is a corner turning memory of a motion parameter estimation path. The memory 18 is configured to store signals responsive to multiple transmissions along a substantially same scan line. The memory 22 is configured to store ultrasound data formatted in an acoustic grid, a Cartesian grid, both a Cartesian coordinate grid and an acoustic grid, or ultrasound data representing a volume in a 3D grid.

The filter 20 is a clutter filter, finite impulse response filter, infinite impulse response filter, analog filter, digital filter, combinations thereof or other now known or later developed filter. In one embodiment, the filter 20 includes a mixer to shift signals to baseband and a programmable low pass filter response for removing or minimizing information at frequencies away from the baseband. In other embodiments, the filter 20 is a low pass, high pass or band pass filter. The filter 20 isolates velocity information from slower moving tissue and reduces velocities from fluids or, alternatively, reduces the influence of data from tissue while maintaining velocity information from fluids. The filter 20 has a set response or may be programmed, such as altering operation as a function of signal feedback or other adaptive process. In yet another embodiment, the memory 18 and/or the filter 20 are part of the flow estimator 22.

The flow estimator 22 is a Doppler processor or cross-correlation processor for estimating the color flow data. In alternative embodiments, another device now known or later developed for estimating velocity, power (e.g., energy), and/or variance from any or various input data may be provided. The flow estimator 22 receives a plurality of signals associated with a substantially same location at different times and estimates a Doppler shift frequency, based on a change or an average change in phase between consecutive signals from the same location. Velocity is calculated from the Doppler shift frequency. Alternatively, the Doppler shift frequency is used as a velocity. The power and variance may also be calculated.

Color flow data (e.g., velocity, power, and/or variance) is estimated for spatial locations in the scan region from the beamformed scan samples. For example, the flow data represents a plurality of different locations in a plane.

The flow estimator 22 may apply one or more thresholds to identify sufficient motion information. For example, velocity and/or power thresholding for identifying velocities is used. In alternative embodiments, a separate processor or filter applies thresholds. In other embodiments, the thresholding is applied after any motions suppression, such as by the processor 24.

The flow estimator 22 outputs frames of data representing the scan region at different times. The beamformed samples for a given flow sample count are used to estimate for a time. A moving window with overlap of the data is used to estimate for other times. Velocities for each location at different times are output.

The processor 24 is a digital signal processor, a general processor, an application specific integrated circuit, field programmable gate array, control processor, digital circuitry, analog circuitry, graphics processing unit, combinations thereof or other now known or later developed device for implementing calculations, algorithms, programming or other functions. The processor 24 operates pursuant to instruction provided in the memory 28, or a different memory for configuring for color Doppler imaging in medical diagnostic ultrasound.

The processor 24 receives color flow data from the flow estimator 22, the memory 28, and/or another source. In one embodiment, the processor 24 implements one or more of the algorithms, acts, steps, functions, methods or processes discussed herein, by processing the data and/or controlling operation of other components of the system 10. Additional or multiple processors may be used to implement various aspects of the algorithms.

The processor 24 or the flow estimator 22 performs phase unwrapping. Alternatively, the velocity scale is set to avoid aliasing.

The processor 24 is configured by software and/or hardware to calculate, for each of the different locations, a value of a parameter. The value is calculated with a function having the energy (e.g., power) and derivatives of velocity samples and/or velocities as variables. Any function may be used. By combining the different types of information into a single parameter, less complex color mapping than multi-parameter maps may be provided. Users may be better able to instinctively understand the flow from images mapped using a single parameter.

The processor 24 performs the mapping. Alternatively, a different processor performs mapping. Using a color map, the values of the parameter are used to look up or determine colors to use for the different locations. The colors are then used as display values to create or generate an image of a two or three-dimensional region of the patient.

The processor 24 is configured to generate a motion image, such as a color flow or Doppler tissue motion image.

The image is generated with the colors mapped from the values of the parameter combined from energy and velocity information. The color or display values are further scan converted, or the processor 24 operates on scan converted motion values.

The memory 28 is video random access memory, random access memory, removable media (e.g. diskette or compact disc), hard drive, database, or other memory device for storing color flow or other motion data, such as velocity and energy data. The stored data is in a polar or Cartesian coordinate format. The memory 28 is used by the processor 24 for the phase unwrapping, calculating, combining, and mapping acts described for FIG. 1. The starting energy and velocity data, processed data including unwrapped velocity values, calculated spatial derivatives of the velocity values, results of the combining of different types of parameters, and/or mapped colors are stored in the memory 28.

The memory 28 also is configured to store the one-dimensional map of colors. The map is stored as a look-up table indexed by the parameter formed using power and velocity information.

The instructions for implementing the processes, methods and/or techniques discussed above are provided on non-transitory computer-readable storage media or memories, such as a cache, buffer, RAM, removable media, hard drive or other computer readable storage media, such as represented by the memory 28. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 27 is a CRT, LCD, plasma, projector, monitor, printer, touch screen, or other now known or later developed display device. The display 27 receives RGB, other color values, or other motion values and outputs an image. The image may be a gray scale or color image. The image represents the region of the patient scanned by the beamformer and transducer 14. The power and velocity are represented in the image using a combined parameter of both.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for Doppler imaging in ultrasound, the method comprising:

acquiring, with an ultrasound scanner, ultrasound data representing a region of a patient;

estimating, with a Doppler processor, powers of flow and velocities of flow from the ultrasound data for each of different locations in the region;

calculating spatial derivatives of the velocities;

combining the spatial derivatives of the velocities with the powers, the combining forming single values where each of the single values is a sum of one of the spatial derivatives of the velocity with one of the powers and with an offset, the offset being set to be greater than a highest positive or negative ones of the spatial derivatives of the velocities to prevent a sign change due to the sum;

mapping results of the combining to colors; and generating an image of the region from the colors.

2. The method of claim 1 wherein acquiring comprises scanning the patient with ultrasound.

3. The method of claim 1 wherein estimating comprises estimating the powers and velocities from Doppler shifts.

4. The method of claim 1 wherein calculating comprises calculating gradients along one or more dimensions.

5. The method of claim 4 wherein calculating the gradients comprises, for each location, calculating the gradients along two dimensions from the location and summing the gradients along the two dimensions for the location, the sum being the spatial derivative of each location.

6. The method of claim 1 wherein calculating comprises calculating the spatial derivative of the velocity for each of the locations, and wherein combining comprises summing, for each of the locations, the power for the location with the spatial derivative for each of the locations.

7. The method of claim 1 wherein combining comprises relatively weighting the spatial derivatives and the powers.

8. The method of claim 1 wherein combining comprises forming one of the single values as the result for each of the locations and wherein mapping comprises mapping only the formed single value to the color for each of the locations.

9. The method of claim 1 wherein combining with the function includes determining the offset as greater than the highest negative value of the spatial derivatives weighted by any weight applied to the spatial derivatives.

10. The method of claim 1 wherein mapping comprises mapping with a one-dimensional color map.

11. The method of claim 1 further comprising:

phase unwrapping the velocities prior to calculating the spatial derivatives.

12. The method of claim 1 wherein combining comprises combining the spatial derivatives, the powers, and the velocities.

13. The method of claim 12 wherein combining comprises combining with relative weighting between the spatial derivatives, powers, and velocities and with an offset.

14. A non-transitory computer readable storage medium having stored therein data representing instructions executable by a programmed processor for Doppler imaging in ultrasound, the storage medium comprising instructions for:

calculating spatial gradients for velocity values estimated for ultrasound scan locations in a patient;

summing the spatial gradients, power values, the velocity values and an offset, the power values estimated for the ultrasound scan locations, the offset being set to be greater than a highest positive or negative one of the spatial gradients or velocity values;

mapping results of the summing to color values; and generating a color flow image with the color values.

15. The non-transitory computer readable storage medium of claim 14 further comprising phase unwrapping the velocity values prior to summing.

16. The non-transitory computer readable storage medium of claim 14 wherein summing comprises weighted summing of the spatial gradients, the power values, the velocity values and the offset.

17. The non-transitory computer readable storage medium of claim 14 wherein mapping comprises mapping with a one-dimensional color map with only positive or only negative values.

18. A system for Doppler imaging in ultrasound, the system comprising:
   a transducer and beamformer for scanning a scan region;
   a Doppler estimator configured to estimate energies and velocity samples of the scan region at different locations, one of the energies and one of the velocity samples being estimated for each of the locations;
   a processor configured to calculate, for each of the different locations, a single value of a parameter that is a sum of the energy for each location and derivative of velocity sample for each location, the derivative of the velocity samples being a local spatial derivative from the velocity samples in a kernel for locations distributed in two or more different directions relative to and including the location, the kernel defining the spatial distribution about the location;
   a memory configured to store a one-dimensional map of colors indexed by the parameter.

19. The system of claim 18 wherein the function includes the velocities as a variable.

\* \* \* \* \*